United States Patent
Pfeifer

(10) Patent No.: US 11,877,915 B2
(45) Date of Patent: Jan. 23, 2024

(54) METHOD OF AND APPARATUS FOR STABILIZING TUCKING-IN SIDE SEAMS OF ABSORBENT HYGIENE PANTS

(71) Applicant: OPTIMA nonwovens GmbH, Schwäbisch Hall (DE)

(72) Inventor: Georg Pfeifer, Schwäbisch Hall (DE)

(73) Assignee: OPTIMA nonwovens GmbH, Schwäbisch Hall (DE)

(*) Notice: Subject to any disclaimer, the term of this patent is extended or adjusted under 35 U.S.C. 154(b) by 0 days.

(21) Appl. No.: 17/614,675

(22) PCT Filed: May 26, 2020

(86) PCT No.: PCT/EP2020/064499
§ 371 (c)(1),
(2) Date: Nov. 29, 2021

(87) PCT Pub. No.: WO2020/239723
PCT Pub. Date: Dec. 3, 2020

(65) Prior Publication Data
US 2022/0226165 A1    Jul. 21, 2022

(30) Foreign Application Priority Data
May 28, 2019  (EP) .................................. 19176956

(51) Int. Cl.
*A61F 13/15* (2006.01)
*A61F 13/496* (2006.01)

(52) U.S. Cl.
CPC .... *A61F 13/15747* (2013.01); *A61F 13/4963* (2013.01); *A61F 2013/15861* (2013.01)

(58) Field of Classification Search
None
See application file for complete search history.

(56) References Cited

U.S. PATENT DOCUMENTS

| | | | |
|---|---|---|---|
| 4,694,978 A | 9/1987 | Westphal et al. | |
| 6,582,543 B1* | 6/2003 | Nilsson ............ | A61F 13/15747 156/476 |
| 10,085,898 B2 | 10/2018 | Fjeldsa | |
| 2002/0123730 A1 | 9/2002 | Popp et al. | |
| 2003/0062113 A1 | 4/2003 | Van Eperen et al. | |
| 2004/0129592 A1 | 7/2004 | Otsubo | |
| 2011/0247747 A1 | 10/2011 | Schneider et al. | |
| 2011/0251038 A1 | 10/2011 | LaVon et al. | |

(Continued)

FOREIGN PATENT DOCUMENTS

EP    3415129 A1 * 12/2018  ............. A61F 13/15

OTHER PUBLICATIONS

Goggle definition of "connect" (Year: 2022).*

(Continued)

*Primary Examiner* — Barbara J Musser
(74) *Attorney, Agent, or Firm* — Akerman LLP

(57) ABSTRACT

The application relates to a method of and an apparatus for tucking a pair of opposing side seams (3, 4) into a body portion (2) of a hygiene pant (1), wherein the side seams (3, 4) are pushed between a front region (20) and a back region (21) of the body portion (2) a distance toward one another, and wherein the tucked side seams (3, 4) are connected in at least one connection region (7) with each other and/or to the body portion (2).

9 Claims, 4 Drawing Sheets

(56) References Cited

U.S. PATENT DOCUMENTS

2014/0378287 A1* 12/2014 Schneider ......... A61F 13/15764
493/405
2016/0374866 A1 12/2016 Schneider

OTHER PUBLICATIONS

International Search Report and Written Opinion of the International Searching Authority issued in connection with PCT/EP2020/064499, dated Jul. 23, 2020.
Search Report issued in connection with European Patent Application No. 19176956.1, dated Sep. 12, 2019.
Office Action dated Apr. 20, 2022 in connection with corresponding Chinese Patent Application No. 202080039497.1.

* cited by examiner

METHOD OF AND APPARATUS FOR STABILIZING TUCKING-IN SIDE SEAMS OF ABSORBENT HYGIENE PANTS

CROSS-REFERENCE TO RELATED APPLICATIONS

This application is a national phase of PCT/EP2020/064499, filed May 26, 2020, and claims priority to European Patent Application No. 19176956.1, filed May 28, 2019, the entire contents of both of which are hereby incorporated by reference.

TECHNICAL FIELD AND PRIOR ART

The present disclosure relates to a method and an apparatus for tucking side seams into a body portion of an absorbent hygiene pant.

The term "hygiene pant" (also referred to as "training pant," "pre-closed diaper," "pant diaper," "pull-on diaper" or simply "pant") refers herein to disposable absorbent articles having a continuous perimeter waist opening and laterally opposing continuous perimeter leg openings designed for infant or adult wearers. A hygiene pant in embodiments is configured and packaged with a continuous or closed waist opening and at least one continuous or closed leg opening, prior to the article being applied to the wearer. In other embodiments, the waist opening is discontinuous and closed when putting on the hygiene pant. As generally known to a person skilled in the art, hygiene pants can be manufactured by various techniques.

WO 03/028608 A1 discloses a method of tucking a pair of opposing refastenable side seams with a resilient component into a body portion of a hygiene pant, comprising the steps of positioning the body portion of the hygiene pant between an upper conveyor having an upper vacuum zone and a lower conveyor having a lower vacuum zone, with the refastenable side seams in a fastened position; holding apart a front region of the body portion from a back region of the body portion using opposing vacuum forces from the upper and lower vacuum zones; pushing the refastenable side seams into the body portion a distance toward one another, creating longitudinal folds in the hygiene pant along outer longitudinal edges of the upper and lower vacuum zones; and compressing the hygiene pant with each of the resilient components pushed into the body portion and in a flat conformation.

SUMMARY OF THE INVENTION

It is the object of the invention to provide an improved method and apparatus for tucking-in side seams into a body portion of a hygiene pant.

This object is solved by the method and the apparatus with the features of claims 1 and 7. Preferred embodiments are defined in the dependent claims.

According to a first aspect, a method of tucking a pair of opposing side seams into a body portion of a hygiene pant is provided, wherein the side seams are pushed between a front region and a back region of the body portion a distance toward one another, and wherein the tucked side seams are connected in at least one connection region to each other and/or to the body portion.

The body portion comprises a front region and a back region, each of which having a waist area and a crotch area, wherein the front region and the back region are connected to each other at the crotch areas. The side seams together with an upper edge of the front region and the back region form a waist opening, and together with side edges of the front region and the back region form two leg openings. The side seams in one embodiment are continuous stripes. In other embodiments, refastenable side seams are provided, which are capable of releasable attachment, separation, and subsequent releasable reattachment without substantial permanent deformation or rupture for at least one cycle. In one embodiment, the side seams are provided with a resilient component. The refastenable side seams in one embodiment are closed prior to being tucked into the body portion. In other embodiments, the side seams are closed simultaneously with a connection of the side seams. In other embodiments, the side seams remain upon and are only closed by a user when putting on the hygiene pant.

The tucked side seams are attached or fixedly connected in at least one connection region to each other and/or to the body portion, so that the side seams tucked into the body portion are fixed in this position.

By fixedly connecting or attaching the side seams to each other and/or to the body portion the folded hygiene pants are stabilized and the side seams remain securely tucked into the body portion during a subsequent packing of the hygiene pants. The hygiene pant with the side seams tucked into the body portion and fixed in this position can be processed in a conventional matter, for example compressed, inserted into a bag etc. without the risk that the side seams become loose again and project from the body portion.

The type of connection and/or the number of connection regions can be suitably chosen by the person skilled in the art such that a disconnection is possible without any inacceptable damaging of the product. In one embodiment, only one connection region at which the side seams have to be disconnected prior to the hygiene pant being applied to a wearer is provided for high user friendliness. In other embodiments, the side seams are disconnected from each other and/or the body portion upon unfolding the hygiene pants without the necessity for the user to apply any disconnection force significantly exceeding forces for unfolding the hygiene pant.

In embodiments of the method, the side seams are connected by using one or more techniques selected from adhesive, e.g. solvent-based adhesive, polymer dispersion adhesive, hot adhesive, contact adhesive, reactive adhesive, ultrasonic techniques, thermal bonding and/or pressure welds. The side seams in one embodiment are directly connected to each other and/or the body portion. In other embodiments, the side seams are connected to each other via a connection patch, bridging a gap between facing side seams.

In embodiments, the side seams are connected to each other and/or to the body portion in a fine connection region, for example along a thin line, and are disconnected by breaking the connection in the connection region.

In alternative or in addition, in another embodiment, the connection region is provided with a predefined breaking area for a manual disconnection upon unfolding the hygiene pant. For example, the connection is provided with a perforated tear line along which the side seams are separated by a user from each other and/or the body portion upon unfolding the hygiene pant.

In one embodiment, the body portion is folded upon tucking the side seams into the body portion. In other embodiments, a pre-folded hygiene pant with projecting side seams is provided and, prior to tucking in the side seams, the pre-folded hygiene pant with projecting side seams is opened by moving the front region and the back region at least in an area of a waist opening apart. In one embodiment, the front region and the back region area are moved apart only in an area of a waist opening. In other embodiments, other areas of the front region and the back region are also moved apart. The area in which the front region and the back region are moved apart is chosen by the person skilled in the art suitably for allowing tucking in the side seams. For opening the pre-folded hygiene pant, in one embodiment, a vacuum force is applied to one or both of the front region and the region. In other embodiments, the pre-folded diaper is opened by a blade entering between the front region and the back region and/or by a blowing device.

In one embodiment, upon pushing the side seams, longitudinal folds with facing crests are created in the side seams. In one embodiment, the side seams contact each other at the crest of the longitudinal folds, wherein the side seams are connected to each other at the crest of the fold. Forming facing crests is in particular advantageous for hygiene pants having side seams which are closed prior to packaging.

In other embodiments, the hygiene pant has unclosed, fastenable side seams with free ends, wherein the free ends are connected to each other and/or to the body portion.

According to a second aspect, an apparatus for tucking a pair of opposing side seams into a body portion of a hygiene pant is provided, the apparatus with a device for pushing the side seams between a front region and a back region of the body portion a distance toward one another, and with a connecting device for connecting the tucked side seams in at least one connection region to each other and/or to the body portion.

In other words, by means of the connecting device the tucked side seams are attached in at least one connection region to each other and/or to the body portion.

The connecting device can be suitably chosen by the person skilled in the art. In embodiments of the invention, the connecting device uses one or more techniques selected from adhesive, e.g. solvent-based adhesive, polymer dispersion adhesive, hot adhesive, contact adhesive, reactive adhesive, ultrasonic techniques, thermal bonding and/or pressure welds.

In embodiments of the apparatus, the device for pushing the side seams between the front region and the back region of the body portion comprises a tucking blade and/or a blowing device. Suitable devices are described for example in WO 3/028608 A1 and/or WO 2011/126743 A1. However, the method and the apparatus are not limited to the use of devices described in these documents.

In embodiments of the apparatus, an opening device is provided for applying a force to a pre-folded hygiene pant with projecting side seams for moving the front region and the back region apart prior to tucking in the side seams is provided. The opening device in embodiments of the apparatus is a vacuum device applying a vacuum force to at least one of the front region and the back region. Suitable devices are described for example in WO 03/028608 A1 and/or WO 2011/126743 A1. However, the method and the apparatus are not limited to the use of devices described in these documents.

BRIEF DESCRIPTION OF THE DRAWINGS

In the following, an embodiment of the invention will be described in detail based on several schematic drawings in which.

DETAILED DESCRIPTION OF EMBODIMENTS OF THE INVENTION

Figure 1:
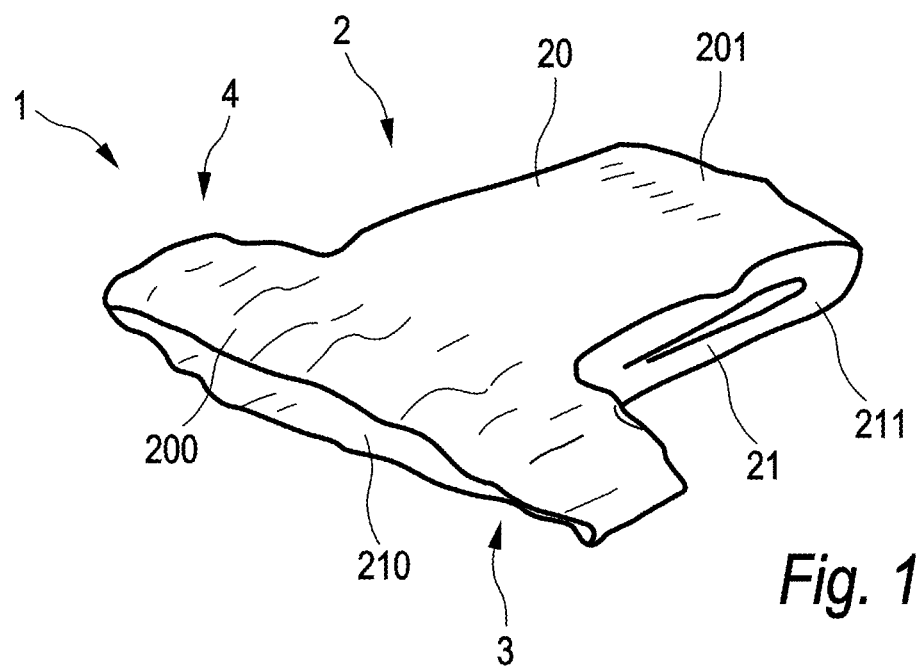
FIG. 1: is a perspective view of a first embodiment of a pre-folded hygiene pant with pair of opposing side seams projecting from a body portion.

Throughout the drawings, the same elements will be denoted by the same reference numerals.

FIG. 1 shows in a perspective view a pre-folded hygiene pant 1. The hygiene pant 1 comprises a body portion 2 with a front region 20 and a back region 21 and two opposing side seams 3, 4 projecting from the body portion 2.

Each of the front region 20 and the back region 21 have a waist area 200, 210 and a crotch area 201, 211, wherein the front region 20 and the back region 21 are connected to each other at the crotch areas 201, 211. The side seams 3, 4 together with an upper edge of the front region 20 and an upper edge of the back region 21 form a waist opening, and together with side edges of the front region 20 and the back region 21 form two leg openings. The side seams 3, 4 in the depicted embodiment are continuous stripes provided with a resilient component. In other embodiments, refastenable side seams are provided, which are capable of releasable attachment, separation, and subsequent releasable reattachment without substantial permanent deformation or rupture for at least one cycle.

The design and shape of the side seams 3, 4 and the body portion 2 of the hygiene pant 1 shown in the figures are only by way of example and various modifications are conceivable. Further, the material and structure of the components of the hygiene pant 1 can be chosen suitably be the person skilled in the art depending on the intended user group of the hygiene pant 1. As generally known, the body portion 2 in embodiments comprises several layers with different properties. The side seams 3, 4 can be formed together with one or both of the front region 20 and the back region 21 and/or joined with the body portion 2.

As generally known, hygiene pants 1 are typically folded prior to a packaging.

As shown in FIG. 1, in the pre-folded state of the hygiene pant 1, the side seams 3, 4 project from the body portion 2. For a further processing of the hygiene pant 1, in particular for packing the hygiene pant 1 into a bag (not shown), the side seams 3, 4 are tucked into the body portion 2 as schematically shown in FIGS. 2 to 5.

Figure 2:
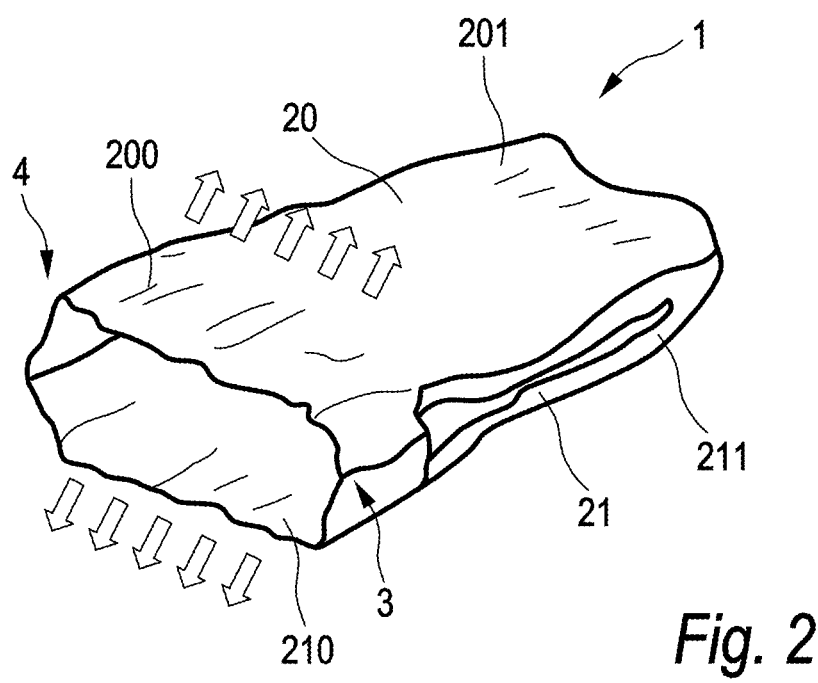
FIG. 2: is a perspective view of the pre-folded hygiene pant of FIG. 1, wherein in an area of the waist opening a front region and a back region of the body portion are moved apart.

In the method shown in FIGS. 2 to 5, the pre-folded hygiene pant 1 is opened by moving the front region 20 and the back region 21 at least in the area of the waist opening apart from one another as shown in FIG. 2. This is achieved in one embodiment by applying a vacuum force on either one of the front region 20 and the back region 21 as schematically indicated by arrows in FIG. 2. However, the invention is not limited to the use of an opening device applying a vacuum force and other opening devices are conceivable for moving the front region 20 and the back region 21 apart from one another. In the embodiment shown, only the waist areas 200, 210 of the front region 20 and the back region 21 are moved apart, whereas the crotch areas 201, 211 of the front region 20 and the back region 21 remain in contact with each other.

Figure 3:
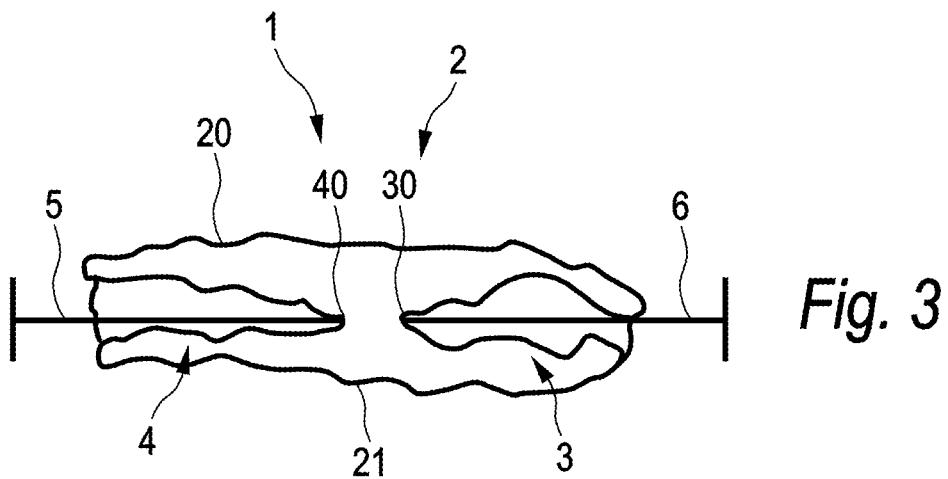
FIG. 3: is a top view (seen from the waist opening) of the pre-folded, opened hygiene pant of FIG. 2, wherein the side seams are pushed between the front region and the back region of the body portion a distance toward one another.
Figure 4:
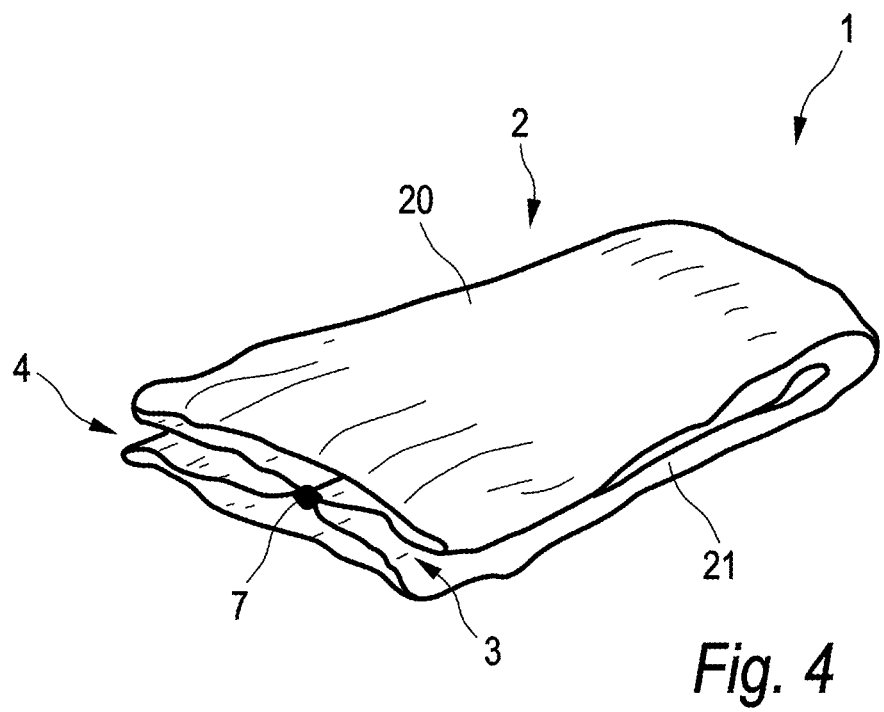
FIG. 4: is a perspective view of the hygiene pant of FIG. 3, wherein the side seams pushed between the front region and the back region of the body portion are connected in a connection region with one another.

Next, the side seams 3, 4 are pushed between the front region 20 and the back region 21 of the body portion 2 a distance toward one another as shown in FIG. 3. In the embodiment shown, two tucking blades 5, 6 are provided for pushing the side seams 3, 4 toward one another. In an alternative embodiment, a blowing device is provided for pushing the two side seams 3, 4 toward one another.

Upon tucking in the side seams 3, 4, longitudinal folds with facing crests 30, 40 are created in the side seams 3, 4. Depending on the length of the side seams 3, 4 and/or a width of the body portion 2, the facing crests 30, 40 of the side seams 3, 4 contact each other or not.

In the embodiment shown, the facing crests of the side seams 3, 4 contact each other and the tucked side seams 3, 4 are connected to each other in a connection region 7 at the crest 30, 40. The connection of the side seams 3, 4 is achieved for example by using one or more techniques selected from adhesive, e.g. solvent-based adhesive, polymer dispersion adhesive, hot adhesive, contact adhesive, reactive adhesive, ultrasonic techniques, thermal bonding and/or pressure welds. In one embodiment, the side seams 3, 4 are directly connected to each other. In other embodiments, in particular in case the crest 30, 40 do not contact each other, a connection patch is provided, wherein the side seams are indirectly connected to each other via the connection patch.

In still another embodiment (not shown), the side seams 3, 4 are not connected to each other, but to the body portion 2.

Figure 5:
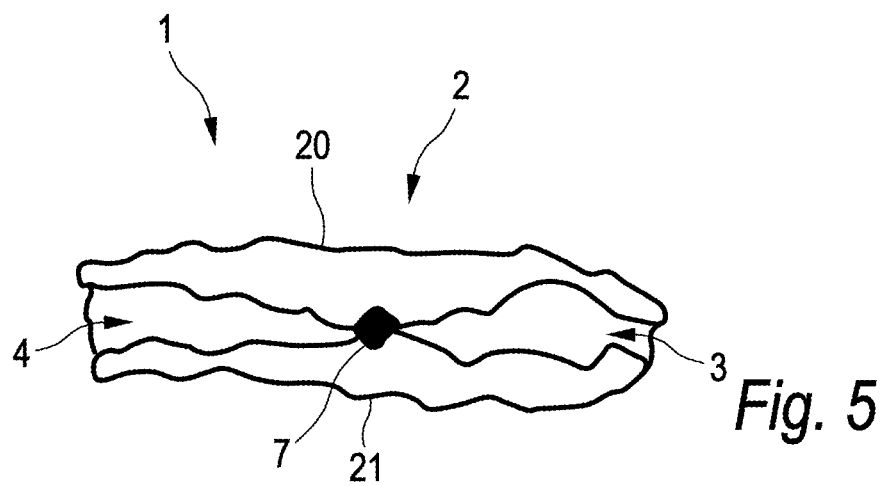
FIG. 5: is a top view of the hygiene pant of FIG. 4, wherein the front region and the back region are moved back toward one another.

After the side seams 3, 4 are connected to each other and/or to the body portion 2, the body portion 2 is closed by moving the front region 20 and the back region 21 back toward each another as shown in FIG. 5. The thus folded hygiene pant 1 with the tucked in and fixed side seams 3, 4 in one embodiment is compressed by advancing the hygiene pant 1 between two conveyor lines (not shown) as generally known by the person skilled in the art.

By connecting the side seams 3, 4 to each other and/or to the body portion 2, it is avoided that the side seams 3, 4 become loose and project from the body portion 2 during a further processing of the hygiene pant 2. The connection is chosen by the person skilled in the art such that the side seams 3, 4 can be easily disconnected from one another and/or from the body portion 2 by a user when unfolding the hygiene pant 1 prior to the hygiene pant 1 being applied to a wearer.

FIGS. 6 to 10 show in perspective views a second embodiment of a pre-folded hygiene pant 1 with a body portion 2 and two opposing side seams 3, 4 projecting from the body portion 2. The body portion 2 has a front region 20 and the back region 21, wherein each of the front region 20 and the back region 21 has a waist area 200, 210 and a crotch area 201, 211, and wherein the front region 20 and the back region 21 are connected to each other at the crotch areas 201, 211. In contrast to the embodiment shown in FIGS. 1 to 5, in the embodiment shown in FIGS. 6 to 10 the side seams 3, 4 are formed integrally with the front region 20 and prior to a use of the hygiene pant 1, the side seams 3, 4 are not attached or connected to the back region 21. In one embodiment, the side seams 3, 4 are capable of releasable attachment to the back region 21, separation, and subsequent releasable reattachment without substantial permanent deformation or rupture for at least one cycle. In other embodiments, the side seams 3, 4 are not releasably attached to the back region 21 when putting on the hygiene pant 1.

Figure 6:
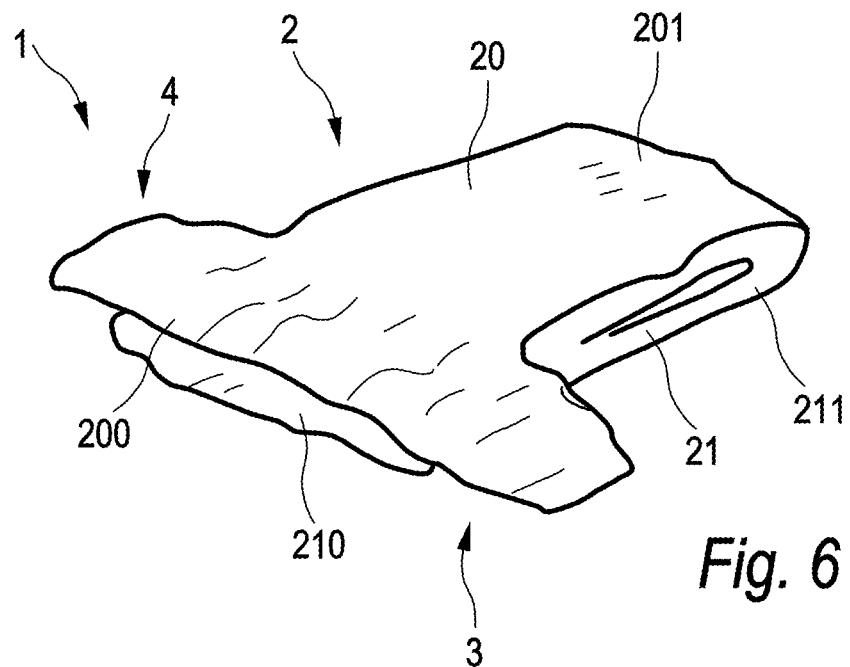
FIG. 6: is a perspective view of a second embodiment of a pre-folded hygiene pant with pair of opposing side seams projecting from a body portion.
Figure 7:
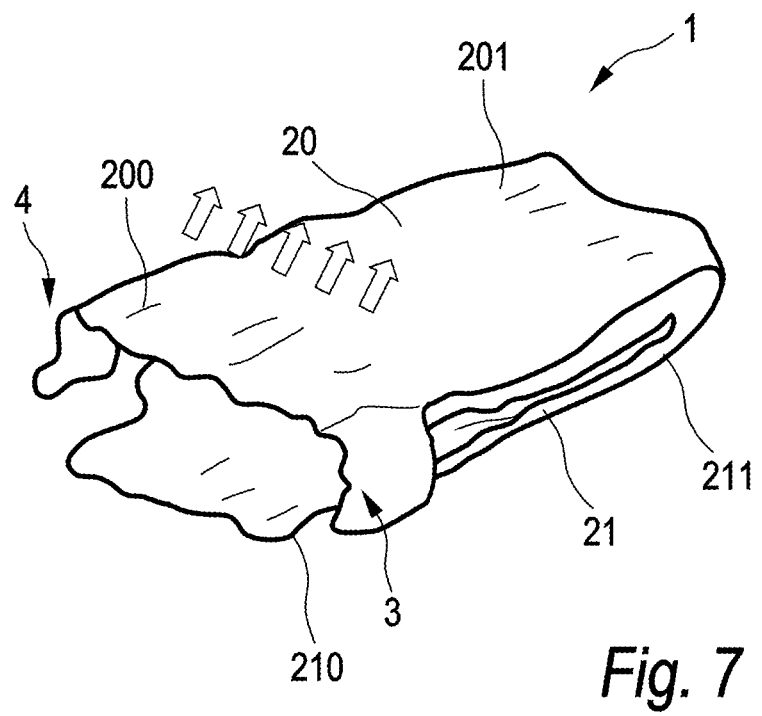
FIG. 7: is a perspective view of the pre-folded hygiene pant of FIG. 6, wherein in an area of the waist opening a front region and a back region of the body portion are moved apart.

For packaging the hygiene pant 1 shown in FIG. 6, the pre-folded hygiene pant 1 is opened by moving the front region 20 and the back region 21 at least in the area of the waist opening apart from one another as shown in FIG. 7. This is achieved in one embodiment by applying a vacuum force on either one of the front region 20 and the back region 21 as schematically indicated by arrows in FIG. 2. However, the invention is not limited to the use of an opening device applying a vacuum force and other opening devices are conceivable for moving the front region 20 and the back region 21 apart from one another. In the embodiment shown, only the waist areas 200, 210 of the front region 20 and the back region 21 are moved apart, whereas the crotch areas 201, 211 of the front region 20 and the back region 21 remain in contact with each other.

Figure 8:
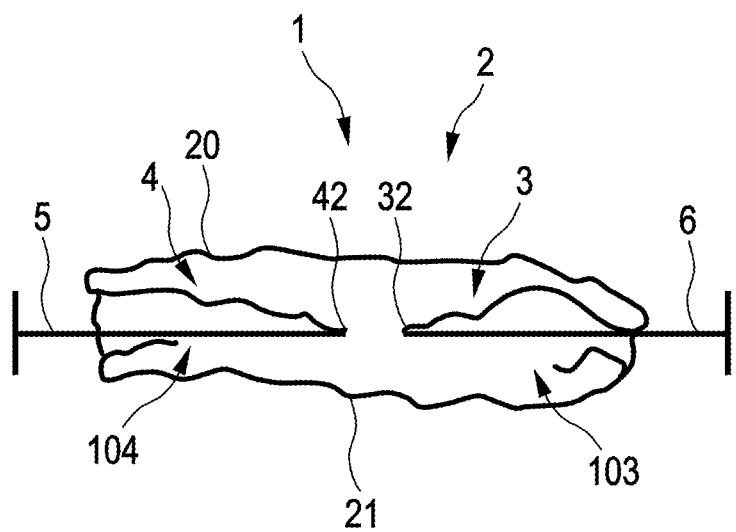
FIG. 8: is a top view (seen from the waist opening) of the pre-folded, opened hygiene pant of FIG. 6, wherein the side seams are pushed between the front region and the back region of the body portion a distance toward one another.
Figure 9:
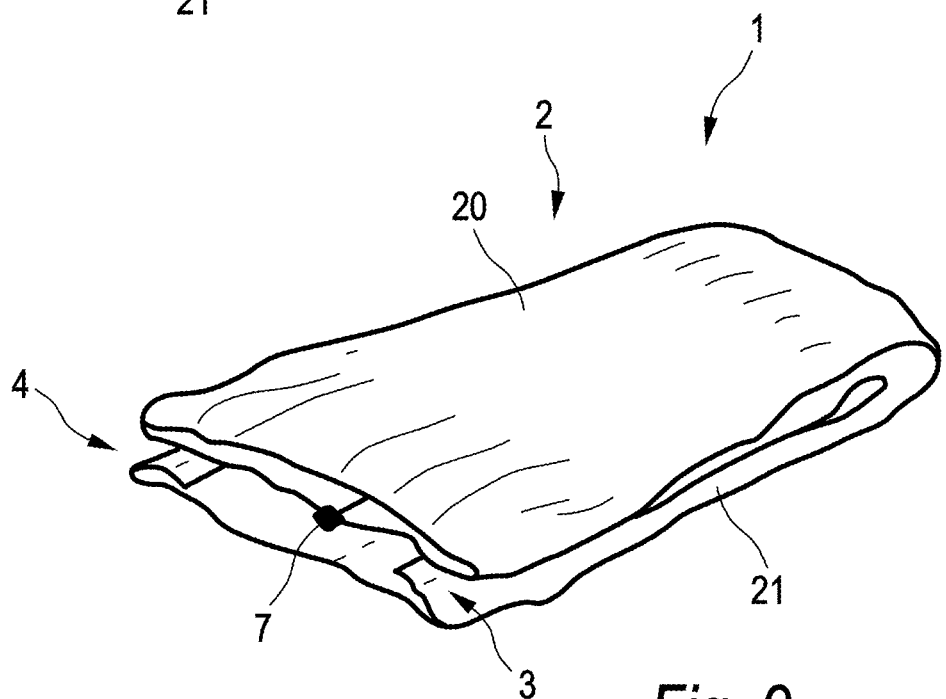
FIG. 9: is a perspective view of the hygiene pant of FIG. 8, wherein the side seams pushed between the front region and the back region of the body portion are connected in a connection region with one another.

Next, the side seams 3, 4 are pushed between the front region 20 and the back region 21 of the body portion 2 a distance toward one another as shown in FIG. 8, for example using two tucking blades 5, 6. As shown in FIG. 8, in the embodiment shown, the back region 21 is provided with two tabs 103, 104, which are also tucked into the body portion 2.

Depending on the length of the side seams 3, 4 and/or a width of the body portion 2, free ends 32, 42 of the side seams 3, 4 contact each other or not.

In the embodiment shown, the free ends 32, 42 of the side seams 3, 4 contact each other and the tucked side seams 3, 4 are connected to each other in a connection region 7 at the free ends 32, 42. The connection of the side seams 3, 4 is achieved for example by using one or more techniques selected from adhesive, e.g. solvent-based adhesive, polymer dispersion adhesive, hot adhesive, contact adhesive, reactive adhesive, ultrasonic techniques, thermal bonding and/or pressure welds. In other embodiments, in particular in case the free ends 32, 42 do not contact each other, a connection patch is provided, wherein the side seams are indirectly connected to each other via the connection patch. In still another embodiment (not shown), the side seams 3, 4 are not connected to each other, but to the body portion 2.

Figure 10:
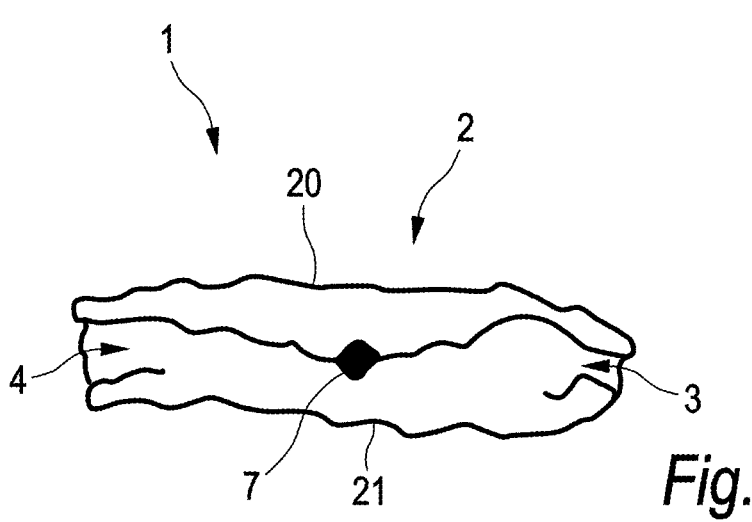
FIG. 10: is a top view of the hygiene pant of FIG. 9, wherein the front region and the back region are moved back toward one another.

After the side seams 3, 4 are connected to each other and/or to the body portion 2, the body portion 2 is closed by moving the front region 20 and the back region 21 back toward each another as shown in FIG. 10.

The invention claimed is:

1. A method of tucking a pair of opposing side seams into a body portion of a hygiene pant,
   wherein the side seams are pushed between a front region and a back region of the body portion a distance toward one another,
   wherein the tucked side seams are fixedly attached or fixedly connected in at least one connection region to each other and/or to the body portion, so that the side seams tucked into the body portion are fixed in this position,
   wherein prior to tucking in the side seams between the front region and the back region of the body portion and fixedly attaching or fixedly connecting the tucked side seams in the at least one connection region to each other and/or to the body portion, for packaging the hygiene pant, a pre-folded hygiene pant with projecting side seams is opened by moving the front region and the back region at least in an area of a waist opening apart.

2. The method according to claim 1, wherein the side seams are connected by using one or more techniques selected from adhesive, solvent-based adhesive, polymer dispersion adhesive, hot adhesive, contact adhesive, reactive adhesive, ultrasonic techniques, thermal bonding and/or pressure welds.

3. The method according to claim 1, wherein the connection region is provided with a predefined breaking area for a manual disconnection upon unfolding the hygiene pant.

4. The method according to claim 1, wherein upon pushing the side seams, longitudinal folds with facing crests are created in the side seams.

5. The method according to claim 1, wherein the hygiene pant has fastenable side seams with free ends, wherein the free ends are connected to each other and/or to the body portion.

6. An apparatus for tucking a pair of opposing side seams into a body portion of a hygiene pant for packaging the hygiene pant,
   with a device for pushing the side seams between a front region and a back region of the body portion a distance toward one another,
   wherein a connecting device is provided for fixedly attaching or fixedly connecting the tucked side seams in at least one connection region to each other and/or to the body portion, so that the side seams tucked into the body portion are fixed in this position,
   wherein an opening device is provided for applying a force to a pre-folded hygiene pant with projecting side seams for moving the front region and the back region at least in an area of a waist opening apart prior to the device tucking in the side seams between the front region and the back region of the body portion and the connecting device fixedly attaching or fixedly connecting the tucked side seams in the at least one connection region to each other and/or to the body portion.

7. The apparatus according to claim 6, wherein the connecting device uses one or more techniques selected from adhesive, solvent-based adhesive, polymer dispersion adhesive, hot adhesive, contact adhesive, reactive adhesive, ultrasonic techniques, thermal bonding and/or pressure welds.

8. The apparatus according to claim 6, wherein the device for pushing the side seams between the front region and the back region of the body portion comprises a tucking blade and/or a blowing device.

9. The apparatus according to claim 6, wherein the opening device is a vacuum device applying a vacuum force to at least one of the front region and the back region.

* * * * *